United States Patent

Wilson et al.

Patent Number: 5,162,188
Date of Patent: Nov. 10, 1992

[54] TONERS AND DEVELOPERS CONTAINING AMIDE-CONTAINING QUATERNARY AMMONIUM SALTS AS CHARGE CONTROL AGENTS

[75] Inventors: John W. Wilson, Rochester; Alexandra D. Bermel, Spencerport, both of N.Y.

[73] Assignee: Eastman Kodak Company, Rochester, N.Y.

[21] Appl. No.: 734,352

[22] Filed: Jul. 18, 1991

[51] Int. Cl.$^5$ .................................. G03G 9/097
[52] U.S. Cl. ............................ 430/110; 430/903
[58] Field of Search .......................... 430/110, 903

[56] References Cited

U.S. PATENT DOCUMENTS 4,239,631  10/1981  Lu ........................... 430/110 X
4,415,646  11/1983  Gruber et al. ............... 430/110

FOREIGN PATENT DOCUMENTS 267059  11/1986  Japan ........................ 430/110
202760   8/1988  Japan ........................ 430/110

Primary Examiner—Roland Martin
Attorney, Agent, or Firm—Willard G. Montgomery

[57] ABSTRACT

New electrostatographic toners and developers are provided containing novel charge control agents comprising amide-containing quaternary ammonium salts having the structure:

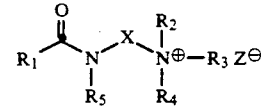

wherein $R_1$ is $C_1$–$C_6$ alkyl or aryl, $R_2$ and $R_3$, which can be the same or different, are alkyl or aryl, $R_4$ is alkyl, aryl or aralkyl, $R_5$ is hydrogen or alkyl, X is $+CH_2)_n$, $Z^\ominus$ is an anion and n is an integer from 2 to 6.

Such amide-containing quaternary ammonium salts also cause toner particles containing them to display lower fusing temperatures and improved paper adhesion indexes.

13 Claims, No Drawings

TONERS AND DEVELOPERS CONTAINING AMIDE-CONTAINING QUATERNARY AMMONIUM SALTS AS CHARGE CONTROL AGENTS

FIELD OF THE INVENTION

This invention relates to certain new electrostatographic toners and developers containing novel amide-containing quaternary ammonium salts which are useful as charge control agents that also serve as adhesion promoters between toner and receiver sheets and as toner fusing temperature reducers.

BACKGROUND OF THE INVENTION

In the art of making and using toner powders, charge control agents are commonly employed to adjust and regulate the triboelectric charging capacity and/or the electrical conductivity characteristics thereof. Many different charge control agents are known which have been incorporated into various binder polymers known for use in toner powders. However, the need for new and improved toner powders that will perform in new and improved copying equipment has resulted in continuing research and development efforts to discover new and improved charge control agents.

Of potential interest are substances which not only serve as toner powder charge control agents, but also function as agents that provide additional results or effects such as promoting adhesion between toner and receiver sheets and as toner fusing temperature reducers. Such multi-functionality offers the potential for achieving cost savings in the manufacture and use of toner powders, developers and copier equipment.

It would, therefore, be desirable to provide new dry electrostatographic toners and developers containing new amide-containing quaternary ammonium salts that could perform the charge-controlling function well in dry, electrostatographic toners and developers as well as promote the adhesion between toner and receiver sheets and, in addition thereto, serve as toner fusing temperature reducers.

SUMMARY OF THE INVENTION

This invention provides new, dry particulate electrostatographic toners and developers containing new charge-control agents comprising amide-containing quaternary ammonium salts having the structure:

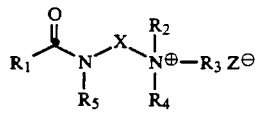

wherein $R_1$ is $C_1$-$C_6$ alkyl or aryl, $R_2$ and $R_3$, which can be the same or different, are alkyl or aryl, $R_4$ is alkyl, aryl or aralkyl, $R_5$ is hydrogen or alkyl, X is $-(CH_2)_n-$, $Z^\ominus$ is an anion and n is an integer from 2 to 6.

The inventive toner powders comprise a polymeric matrix phase or polymeric binder which has dispersed therein at least one quaternary ammonium salt having incorporated therein at least one amide moiety that is bonded through an alkylene linking group to a quaternary ammonium nitrogen atom.

When incorporated into toner powders, such quaternary ammonium salts not only function as good charge control agents, but also serve as toner powder fusing temperature depressants and paper adhesion promoters.

These salts are preferably dispersed in the polymeric binder matrix phase comprising the core or body portion of a toner particle.

Toner powders containing these salts can also be mixed with a carrier vehicle to form electrostatographic developers.

Toner powders containing these salts incorporated into the polymeric binder thereof can be used for producing developed toned images on a latently imaged photoconductor element, for transfer of the toned image from the photoconductor element to a receiver sheet and for heat fusion of the toned image on the receiver while employing processes and processing conditions heretofore generally known to the art of electrophotography.

Various other advantages, aims, features, purposes, embodiments and the like associated with the present invention will be apparent to those skilled in the art from the present specification taken with the accompanying claims.

DESCRIPTION OF THE PREFERRED EMBODIMENTS

(A) Definitions

The term "particle size" as used herein, or the term "size", or "sized" as employed herein in reference to the term "particles", means volume weighted diameter as measured by conventional diameter measuring devices, such as a Coulter Multisizer, sold by Coulter, Inc. Mean volume weighted diameter is the sum of the mass of each particle times the diameter of a spherical particle of equal mass and density, divided by total particle mass.

The term "glass transition temperature" or "Tg" as used herein means the temperature at which a polymer changes from a glassy state to a rubbery state. This temperature (Tg) can be measured by differential thermal analysis as disclosed in "Techniques and Methods of Polymer Evaluation", Vol. 1, Marcel Dekker, Inc., N.Y., 1966.

The term "melting temperature" or "Tm" as used herein means the temperature at which a polymer changes from a crystalline state to an amorphous state. This temperature (Tm) can be measured by differential thermal analysis as disclosed in "Techniques and Methods of Polymer Evaluation".

The term "adhesion index" as used herein is a measure of toner adhesion to paper after the toner has been fused. The adhesion index test involves adhering a metal block to a toner patch and measuring the energy required to cause interfacial failure between the toner layer and its contacting substrate by collision of a pendulum with the metal block. The range of adhesion index is from 0 units (no adhesion of toner to substrate) to 100 units (excellent adhesion of toner to substrate).

(B) Amide-Containing Quaternary Ammonium Salts

This invention is directed to new, dry particulate electrostatographic toners and developers containing amide-containing quaternary ammonium salts of the formula:

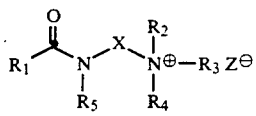

wherein $R_1$ is $C_1$–$C_6$ alkyl or aryl, $R_2$ and $R_3$ which can be the same or different, are alkyl or aryl, $R_4$ is alkyl, aryl or aralkyl, $R_5$ is hydrogen or alkyl, X is $-(CH_2)_n$, $Z^{\ominus}$ is an anion and n is an integer from 2 to 6.

As used herein, the term "alkyl" includes straight and branched chain alkyl groups and cycloalkyl groups.

As used herein, the term "anion" refers to negative ions such as m-nitrobenzenesulfonate, tosylate, tetraphenylborate, dicyanamide, chloride and the like.

As used herein, the term aryl includes phenyl, naphthyl, anthryl and the like.

As used herein, the term "aralkyl" includes benzyl, naphthylmethyl and the like.

Alkyl and aryl groups can be unsubstituted or substituted with a variety of substituents such as alkoxy, halo or other groups.

Illustrative examples of amide-containing quaternary ammonium salts useful in the present invention include, for example:

N,N-dimethyl-N-(2-benzoylaminoethyl)-benzylammonium m-nitrobenzenesulfonate;
N,N-dimethyl-N-(2-benzoylaminoethyl)-benzylammonium chloride;
N,N-dimethyl-N-(2-acetylaminoethyl)-benzylammonium m-nitrobenzenesulfonate;
N,N-dimethyl-N-(2-benzoylaminoethyl)-N-(2-naphthmethyl)benzylammonium dicyanamide;
N,N-dimethyl-N-(3-benzoylaminopropyl)benzylammonium tetraphenylborate;
N,N-diethyl-N-[2-(2-naphthoylamino)ethyl]benzylammonium tosylate;
N,N-diphenyl-N-(2-benzoylaminoethyl)-benzylammonium chloride;
N,N-di(2-naphthyl)-N-(2-benzoylaminoethyl)-benzylammonium tetraphenylborate;
N-(2-benzoylaminoethyl)trimethylammonium m-nitrobenzenesulfonate;
N,N-dimethyl-N-(2-benzoylaminoethyl)anilinium tetraphenylborate, and
N,N,-dimethyl-N-[2-(N-benzoyl-N-methyl)-aminoethyl]benzylammonium tetraphenylborate.

A presently preferred salt for use in the toners and developers of the present invention is an amide-containing quaternary ammonium salt of the invention wherein in the formula set forth above $R_1$ is phenyl, $R_2$ is methyl, $R_3$ is methyl, $R_4$ is benzyl, $R_5$ is hydrogen, n is 2 and $Z^{\ominus}$ is m-nitrobenzenesulfonate.

(C) Synthesis

The amide-containing quaternary ammonium salts employed in the toners and developers of the present invention can be prepared by any convenient route. One general route is to acylate a N,N-di(loweralkyl)alkylenediamine with an acid chloride to produce the corresponding (N,N-di(loweralkyl)amino)-alkyl amide which is subsequently quaternized with a reactive aliphatic halide. The quaternary ammonium salt is converted to the desired salt by a metathesis or ion exchange reaction with a reactive alkali metal arylsulfonate or other acid salt.

Preferably, the acid chloride is benzoyl chloride, while the N,N-di(loweralkyl)alkylenediamine is N,N-dimethylethylenediamine. In place of the acid chloride, the corresponding carboxylic acid can be employed.

One convenient and presently preferred procedure for such an amide preparation is to prepare a basic aqueous solution of the N,N-di(loweralkyl)-alkylenediamine. To this solution is slowly added a solution of the acid chloride in a water immiscible organic solvent, methylene chloride being presently preferred. The addition is preferably accompanied by rapid stirring. The mole ratio of N,N-di(loweralkyl)-alkylenediamine to total added acid chloride is preferably about 1:1. The ensuing reaction is exothermic and, after the reaction is complete, stirring is preferably continued for a time period, such as at least about 4.5 hours. The organic layer is then separated, washed with water and dried, preferably over $MgSO_4$ or the like, and concentrated. The product is typically an oil which can be purified by distillation.

One convenient and presently preferred procedure for the preparation of the quaternary ammonium salt is to prepare the amide and the quaternizing agent as solutes in the same highly polar solvent, acetonitrile being one presently particularly preferred example. The mole ratio of amide compound to the quaternizing agent is preferably about 1:1. Such a solution is then heated at reflux for a time in the range of from about 15 to 20 hours. The reaction mixture is then concentrated by solvent evaporation to yield an oil or a crystalline solid. The product can be used without further purification for the next step in the synthesis, or the product can be purified by recrystallization, for example, from a ketone, such as 2-butanone, or the like, followed by washing and drying.

One convenient and presently preferred procedure for preparation of the quaternary ammonium organic salt from the intermediate halide is to dissolve the ion exchange agent in water and add this solution to a second aqueous solution containing the quaternary ammonium salt intermediate. The mole ratio of such salt to such ion exchange agent should be about 1:1. Typically, a precipitate is formed immediately which is in the form of an oil. The oil is water washed (preferably with distilled or deionized water), and then dissolved in a water immiscible organic solvent, such as methylene chloride, or the like. The water layer is separated, the organic layer is dried over $MgSO_4$, or the like, and the product thereby concentrated. The resulting product can be crystallized with ligroine and recrystallized from an alkanol, such as isopropanol, or the like, if desired.

(D) Toners And Toner Preparation

To be utilized as a charge-control agent in the electrostatographic toners of the invention, the quaternary ammonium salts are incorporated into toner particles. For present purposes, toner particles can be regarded as being preferably comprised on a 100 weight percent basis of:

(a) about 0.5 to about 10 weight percent of at least one quaternary ammonium salt;
(b) about 75 to about 97.5 weight percent of a thermoplastic polymer; and
(c) about 2 to about 15 weight percent of a colorant.

The size of the toner particles is believed to be relatively unimportant from the standpoint of the present invention; rather the exact size and size distribution is influenced by the end use application intended. So far as now known, the toner particles can be used in all known electrostatographic copying processes. Typically and illustratively, toner particle sizes range from about 0.5 to about 100 microns, preferably from about 4 to about 35 microns.

The properties of the thermoplastic polymers employed as the toner matrix phase materials in the present invention can vary widely. Typically, and preferably, amorphous toner polymers having a glass transition temperature in the range of about 50° to about 120° C. or blends of substantially amorphous polymers with substantially crystalline polymers having a melting temperature in the range of about 65° to about 200° C. are utilized in the present invention. Preferably, such polymers have a number average molecular weight in the range of about 1,000 to about 500,000. The weight average molecular weight can vary, but preferably is in the range of about $2 \times 10^3$ to about $10^6$. Typical examples of such polymers include polystyrene, polyacrylates, polyesters, polyamides, polyolefins, polycarbonates, phenol formaldehyde condensates, alkyd resins, polyvinylidene chlorides, epoxy resins, various copolymers of the monomers used to make these polymers, such as polyesteramides, acrylonitrile copolymers with monomers, such as styrene, acrylics, and the like.

Preferably, the thermoplastic polymers used in the practice of this invention are substantially amorphous. However, as indicated above, mixtures of polymers can be employed, if desired, such as mixtures of substantially amorphous polymers with substantially crystalline polymers.

Presently preferred polymers for use in toner powders are styrene/n-butyl acrylate copolymers. In general, preferred styrene/n-butyl acrylate copolymers have a glass transition temperature (Tg) in the range of about 50° to about 100° C.

An optional but preferred starting material for inclusion in such a blend is a colorant (pigment or dye). Suitable dyes and pigments are disclosed, for example, in U.S. Reissue Patent No. 31,072, and in U.S. Pat. Nos. 4,140,644; 4,416,965; 4,414,152; and 2,229,513. One particularly useful colorant for the toners to be used in black and white electrophotographic copying machines is carbon black. When employed, colorants are generally employed in quantities in the range of about 1 to about 30 weight percent on a total toner powder weight basis, and preferably in the range of about 2 to about 15 weight percent.

Toner compositions, if desired, can also contain other additives of the types which have been heretofore employed in toner powders, including leveling agents, surfactants, stabilizers, and the like. The total quantity of such additives can vary. A present preference is to employ not more than about 10 weight percent of such additives on a total toner powder composition weight basis.

Various procedures are known to the art for incorporating additives, such as the quaternary ammonium salts used in the present invention, colorants, or the like, into a desired polymer or mixture of polymers. For example, a preformed mechanical blend of particulate polymer particles, quaternary ammonium salts, colorants, etc., can be roll milled or extruded at a temperature sufficient to melt blend the polymer or mixture of polymers to achieve a uniformly blended composition. Thereafter, the cooled composition can be ground and classified, if desired, to achieve a desired toner powder size and size distribution.

Preferably, prior to melt blending, the toner components, which preferably are preliminarily placed in a particulate form, are blended together mechanically. With a polymer having a Tg in the range of about 50° to about 120° C., or a Tm in the range of about 65° to about 200° C., a melt blending temperature in the range of about 90° to about 240° C. is suitable using a roll mill or extruder. Melt blending times (that is, the exposure period for melt blending at elevated temperatures) are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification, if employed, can be conventionally accomplished using one or two steps.

In place of melt blending, the polymer can be dissolved in a solvent and the additives dissolved and/or dispersed therein. Thereafter, the resulting solution or dispersion can be spray dried to produce particulate toner powders.

Limited coalescence polymer suspension procedures, are particularly useful for producing small sized, uniform toner particles, such as toner particles under about 10 microns in size.

The toner powders used in this invention preferably have a fusing temperature latitude in the range of about 275° to about 400° F., although toner powders with higher and lower fusing temperatures can be prepared and used. The toner powders characteristically display excellent paper adhesion characteristics. Typically, the toner powders have a paper adhesion index value in the range of about 30 to about 100, although toner powders with lower such values can be prepared and used. Paper adhesion index values of such toner powders are characteristically higher than those of toner powders prepared with the same polymer and additives but containing a quaternary ammonium salt not of this invention and are comparable to a toner powder prepared with the same polymer and additives but containing no charge control agent.

To be utilized as toners in electrostatographic developers of the invention, toners containing the aforedescribed salts can be mixed with a carrier vehicle. The carrier vehicles which can be used to form such developer compositions can be selected from a variety of materials. Such materials include carrier core particles and core particles overcoated with a thin layer of film-forming resin.

The carrier core materials can comprise conductive, non-conductive, magnetic, or non-magnetic materials. For example, carrier cores can comprise glass beads; crystals of inorganic salts such as aluminum potassium chloride; other salts such as ammonium chloride or sodium nitrate; granular zircon; granular silicon; silicon dioxide; hard resin particles such as poly(methyl methacrylate); metallic materials such as iron, steel, nickel, carborundum, cobalt, oxidized iron; or mixtures or alloys of any of the foregoing. See, for example, U.S. Pat Nos. 3,850,663 and 3,970,571. Especially useful in magnetic brush development schemes are iron particles such as porous iron particles having oxidized surfaces, steel particles, and other "hard" or "soft" ferromagnetic materials such as gamma ferric oxides or ferrites, such as ferrites of barium, strontium, lead, magnesium, or aluminum. See, for example, U.S. Pat. Nos. 4,042,518; 4,478,925; and 4,546,060.

As noted above, the carrier particles can be overcoated with a thin layer of a film-forming resin for the purpose of establishing the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Other useful resins are fluorocarbons such as polytetrafluoroethylene, poly(vinylidene fluoride), mixtures of these, and copolymers of vinylidene fluoride and tetrafluoroethylene. See, for example, U.S. Pat. Nos. 4,545,060; 4,478,925; 4,076,857; and 3,970,571. Such polymeric fluorohydrocarbon carrier coatings can serve a number of known purposes. One such purpose can be to aid the developer to meet the electrostatic force requirements mentioned above by shifting the carrier particles to a position in the triboelectric series different from that of the uncoated carrier core material, in order to adjust the degree of triboelectric charging of both the carrier and toner particles. Another purpose can be to reduce the frictional characteristics of the carrier particles in order to improve developer flow properties. Still another purpose can be to reduce the surface hardness of the carrier particles so that they are less likely to break apart during use and less likely to abrade surfaces (e.g., photoconductive element surfaces) that they contact during use. Yet another purpose can be to reduce the tendency of toner material or other developer additives to become undesirably permanently adhered to carrier surfaces during developer use (often referred to as scumming). A further purpose can be to alter the electrical resistance of the carrier particles.

A typical developer composition containing the above-described toner and a carrier vehicle generally comprises from about 1 to about 20 percent by weight of particulate toner particles and from about 80 to about 99 percent by weight carrier particles. Usually, the carrier particles are larger than the toner particles. Conventional carrier particles have a particle size on the order of from about 20 to about 1200 microns, preferably 30–300 microns.

Alternatively, the toners of the present invention can be used in a single component developer, i.e., with no carrier particles.

The toner and developer compositions of this invention can be used in a variety of ways to develop electrostatic charge patterns or latent images. Such developable charge patterns can be prepared by a number of means and be carried for example, on a light sensitive photoconductive element or a non-light-sensitive dielectric-surface element such as an insulator-coated conductive sheet. One suitable development technique involves cascading the developer composition across the electrostatic charge pattern, while another technique involves applying toner particles from a magnetic brush. This latter technique involves the use of a magnetically attractable carrier vehicle in forming the developer composition. After imagewise deposition of the toner particles, the image can be fixed, e.g., by heating the toner to cause it to fuse to the substrate carrying the toner. If desired, the unfused image can be transferred to a receiver such as a blank sheet of copy paper and then fused to form a permanent image.

The invention is further illustrated by the following Examples. In these Examples, all melting points and boiling points are uncorrected. NMR (nuclear magnetic resonance) spectra were obtained with a Varian Gemini-200 NMR spectrometer. All elemental analyses were performed by combustion. Unless otherwise indicated, all starting chemicals were commercially obtained.

EXAMPLES

Example 1

Preparation of N-(2-Dimethylaminoethylbenzamide

A solution of 79.73 grams (0.567 mol) of benzoyl chloride in 320 milliters of methylene chloride was added to a solution of 50.0 grams (0.567 mol) of N,N-dimethylethylenediamine, 22.68 grams (0.567 mol) of sodium hydroxide and 320 milliters of water over a period of 15 minutes with rapid stirring. The mixture was then stirred for another 4.5 hours and the organic layer was separated, washed with water, dried over magnesium sulfate and concentrated. The residue was distilled to give 54.5 grams (50.0% of theory) of product; bp=139°–143° C./0.7 mm.

Anal. Calcd. for $C_{11}H_{16}N_2O$: C,68.72;H,8.39; N,14.57; Found: C,67.06;H,7.96;N,13.61.

NMR agreed With the proposed structure.

This material was sufficiently pure for use in subsequent steps.

Example 2

Preparation of N,N-Dimethyl-N-(2-benzoylaminoethyl)benzylammonium Chloride

A solution of 19.23 grams (0.10 mol) of the N-(2-dimethylaminoethyl)benzamide, prepared as described in Example 1, 12.66 grams (0.10 mol) of α-chlorotoluene and 64 milliters of acetonitrile was heated at reflux for 19.75 hours. Solid crystallized on cooling which was collected, washed with acetonitrile and dried. The yield of product was 24.0 grams (75.27% of theory); mp=175°–176° C.

Anal. calcd. for $C_{18}H_{23}ClN_2O$: C,67.81;H,7.27;Cl,11.12%;N,8.79%. Found: C,67.80;H,7.18;Cl,11.00;N,8.82.

NMR agreed With the proposed structure.

Example 3

Preparation of N,N-Dimethyl-N-(2-benzoylaminoethyl)benzylammonium m-Nitrobenzenesulfonate A solution of 11.26 grams (0.05 mol) of sodium m-nitrobenzenesulfonate in 50 milliters of water was added to a solution of 15.94 grams (0.05 mol) of the N,N-dimethyl-N-(2-benzoylaminoethyl)benzylammonium chloride, prepared as described in Example 2, in 50 milliters of water. An oily precipitate formed. The water layer was decanted and the oil was rinsed with water, dissolved in methylene chloride, dried over magnesium sulfate and concentrated to a viscous oil. The oil was treated with ligroine (bp=35°–60° C.) with warming. The oil crystallized and the solid formed was collected and recrystallized from isopropanol. The yield of product was 10.75 grams (44.28% of theory); mp=109°–112° C.

Anal. calcd. for $C_{24}H_{27}N_3O_6S$: C,59.37;H,5.60;N,8.65%;S,6.60. Found: C,59.12;H,5.62;N,8.70;S,7.00.

NMR agreed with the proposed structure.

Example 4

Toner Powder Preparation (Dry Weight Basis)

A styrene/n-butyl acrylate copolymer was obtained by limited coalescence polymerization and blended with the additive components identified in the following Table I in the amounts set forth therein.

TABLE I

| Component | Blend A pph[1] | Blend B pph[1] | Blend C pph[1] |
|---|---|---|---|
| Styrene/n-butyl acrylate | 100 | 100 | 100 |
| Carbon black | 6 | 6 | 6 |
| Charge control agent: | | | |
| A. None | 0 | 0 | 0 |
| B. N,N-dimethyl-N-(2-benzoylaminoethyl)-benzyl-ammonium m-nitrobenzenesulfonate (formulation of Example 3) | 0 | 1 | 0 |
| C. N-octadecyl-N,N-dimethylbenzyl-ammonium m-nitrobenzenesulfonate | 0 | 0 | 1 |

[1]Parts by Weight

The carbon black was "Regal TM 300". Each blend was roll milled at 150° C. for 20 minutes, cooled, crushed and classified to produce a toner powder product having a size of about 12 microns and a size distribution of about 2-30 microns. The charge control agent identified in Table I above as N-octadecyl-N,N-dimethylbenzylammonium m-nitrobenzenesulfonate was utilized for comparative purposes.

Example 5:

Fusing And Adhesion Performance

Each of the styrene/n-butyl acrylate toner powder Blends A, B and C were evaluated on a fusing breadboard consisting of a fusing roller coated with 100 mils of red rubber, engaged at constant speed and pressure onto a backup roller coated with polytetrafluoroethylene (available commercially as Silverstone TM from E.I. duPont de Nemours and Co.) Both roller surfaces were coated by hand with a release oil (60,000 centistoke polydimethylsiloxane oil available from Dow Corning Co.). The nip width between the two rollers was 0.215-0.240 inch and the fuser was operated at 12.25 inches/second. The fusing temperature was 350° F. Six longitudinally extending stripes of toner were applied to the wire side of Kodak alkaline DP paper, and the toned papers were run through the fusing breadboard. The transmission density of the toned, fused stripes was between 1.2 and 1.5.

The adhesion index was determined for each stripe, and the results for each of the various toner Blends A, B and C are presented in Table II below.

TABLE II

| Blend | Charge Control Agent | Average Adhesion Index (AI) of Toner |
|---|---|---|
| A | none | 69 |
| B | N,N-dimethyl-N-(2-benzoyl-aminoethyl)benzylammonium m-nitrobenzenesulfonate | 71 |
| C | N-octadecyl-N,N-dimethyl-benzylammonium m-nitro-benzenesulfonate | 37 |

The adhesion index values are the average of 8 measurements and the standard deviations are less than 7 units for the measurements. The toner containing the ammonium salt with the amide moiety had a significantly higher adhesion index than the toner containing the N-octadecyl-N,N-dimethylbenzylammonium m-nitrobenzenesulfonate charge control agent, and had comparable adhesion index to the toner without a charge control agent.

This invention has been described in detail with particular reference to preferred embodiments thereof, but it will be understood that variations and modifications can be effected within the spirit and scope of the invention.

We claim:

1. A dry, particulate electrostatographic toner composition comprising a polymeric binder and a charge control agent comprising an amide-containing quaternary ammonium salt having the structure:

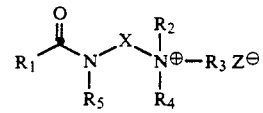

wherein $R_1$ is $C_1$–$C_6$ alkyl or phenyl, $R_2$ and $R_3$, which can be the same or different, are alkyl or aryl, $R_4$ is alkyl, aryl or aralkyl, $R_5$ is hydrogen or alkyl, X is $-(CH_2)_n-$, $Z^\ominus$ is an anion and n is an integer from 2 to 6.

2. The toner composition of claim 1, wherein said salt is N,N-dimethyl-N-(2-benzoylaminoethyl)-benzylammonium m-nitrobenzenesulfonate.

3. The toner composition of claim 1, wherein said salt is N,N-dimethyl-N-(2-acetylaminoethyl)-benzylammonium m-nitrobenzenesulfonate.

4. The toner composition of claim 1, wherein said salt is N,N-dimethyl-N-(3-benzoylaminopropyl)-benzylammonium tetraphenylborate.

5. The toner composition of claim 1, wherein said salt is N,N-dimethyl-N-(2-benzoylaminoethyl)-N-(2-naphthylmethyl)benzylammonium dicyanamide.

6. The toner composition of claim 1, wherein said salt is N,N-diphenyl-N-(2-benzoylaminoethyl)-benzylammonium chloride.

7. The toner composition of claim 1, wherein said salt is N,N-di(2-naphthyl)-N-(2-benzoylaminoethyl)benzylammonium tetraphenylborate.

8. The toner composition of claim 1, wherein said salt is N-(2-benzoylaminoethyl)trimethylammonium m-nitrobenzenesulfonate.

9. The toner composition of claim 1, wherein said salt is N,N-dimethyl-N-(2-benzoylaminoethyl)anilinium tetraphenylborate.

10. The toner composition of claim 1, wherein said salt is N,N,-dimethyl-N-[2-(N-benzoyl-N-methyl-)aminoethyl]benzylammonium tetraphenylborate.

11. The toner composition of claim 1, wherein said salt is N,N-dimethyl-N-(2-benzoylaminoethyl)benzylammonium chloride.

12. An electrostatographic developer comprising (a) the particulate toner composition of claim 1 and (b) carrier particles.

13. The developer of claim 12, wherein the carrier particles comprise core material coated with a fluorohydrocarbon polymer.

* * * * *

UNITED STATES PATENT AND TRADEMARK OFFICE
CERTIFICATE OF CORRECTION

PATENT NO. : 5,162,188
DATED : November 10, 1992
INVENTOR(S) : John C. Wilson, et al It is certified that error appears in the above-indentified patent and that said Letters Patent is hereby corrected as shown below:

On title page, item [75] "John W. Wilson" should be --John C. Wilson--

Signed and Sealed this

Twenty-seventh Day of September, 1994

Attest:

Attesting Officer

BRUCE LEHMAN

Commissioner of Patents and Trademarks